Dec. 29, 1953 J. F. DUKE, SR., ET AL Plant Pat. 1,236
PEACH TREE
Filed Sept. 17, 1951
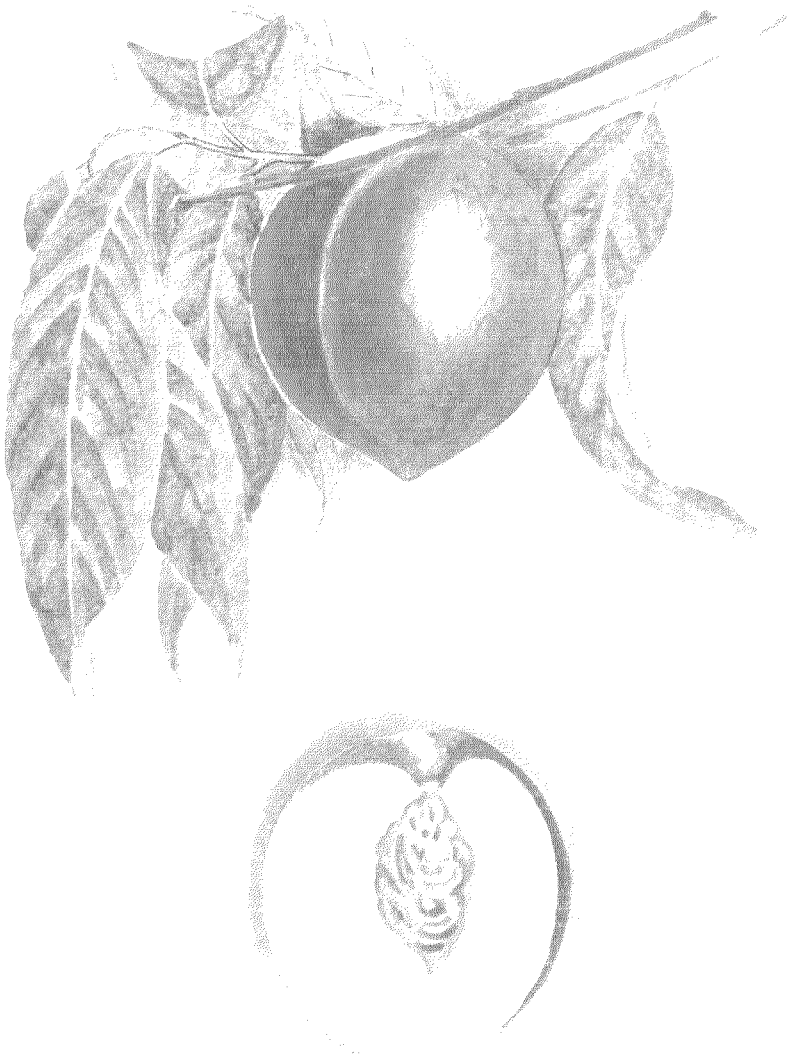
WITNESS
Addison E. Avery
INVENTORS
John F. Duke, Sr.
John F. Duke, Jr.
Leman P. Duke
Wilfred L. Lawson
ATTY.

Patented Dec. 29, 1953

Plant Pat. 1,236

UNITED STATES PATENT OFFICE 1,236

PEACH TREE

John F. Duke, Sr., John F. Duke, Jr., and
Leman P. Duke, Fort Valley, Ga.

Application September 17, 1951, Serial No. 246,924

1 Claim. (Cl. 47—62)

Our present invention relates to a new and improved peach tree of an early ripening variety, which has distinct and advantageous differences from similar varieties.

The improved peach tree herein described grew and was located in our orchard comprising 4,000 Dixired and 7,000 Erly-Red-Fre trees.

The locating of this new variety came about as a result of our practice of patrolling, or carefully riding at frequent intervals, block after block of our orchards, comprising some 100,000 peach trees, on the lookout by careful inspection of the trees, for new mutations or sports. Such inspections begin at budding time and last, or continue, until maturity.

While it is not known with certainty, it is believed that the present new variety is a mutation of a variety in the orchard block in which it developed, such as the Dixired (not patented) or Erly-Red-Fre, Patent No. 320. It is believed that such mutation probably occurred at the time of budding and presumably upon an Erly-Red-Fre parent tree. Such bud therefore, it is believed, originated the present tree as a sport, from which reproductions have been taken as hereinafter set forth.

In the drawing:

Figure 1 is a view in elevation of the herein described new variety of peach showing the fully tree ripened form thereof.

Figure 2 is a view of the inside of one-half of the peach showing the extent of coloring of the meat and the nature of the stone.

The particular or special characteristics distinguishing the present new peach from other so-called early varieties, such, for example, as the Mayflower, Dixired, Erly-Red-Fre and Dixie are that it requires less chilling hours under 45° F. than such varieties which require from 900 to 1200 chilling hours. The last named varieties are not known to be patented.

The present new variety requires only the same number of chilling hours as the Early Hiley (not patented) and the Pearson Hiley (Patent No. 760) varieties, which is from 500 to 600 hours.

The present new peach is of the freestone type and ripens earlier than any known freestone type peach. For example when this new type peach was first observed on May 31, 1949, no peach shipment had been made from the State of Georgia and this new peach, on that date was fully matured. Again on June 5, 1950, when all the peaches of this new variety were ripe not a single shipment of peaches had been made from Georgia.

The following is a detailed description of the new variety, with color terminology in accordance with ordinary dictionary definition as well as in accordance with the Maerz and Paul Dictionary of Color.

Tree: Medium size; vigorous; upright; dense; regular bearer.

Trunk: Stocky; smooth.

Branches: Stocky.

Twigs: Brownish to green. Lenticels—many; medium size.

Leaves:

*Length.*—5½ to 6 inches.

*Width.*—Average 1 inch; lanceolate; pointed; thick; dark green; smooth; serrate. The top surface of the leaf approaches the color of plate 23, letter L, numeral 7, while the undersurface approaches the color of Plate 21, letter H, numeral 6. Maerz and Paul Dictionary.

*Petiole.*—Medium thick; medium long.

*Glands.*—Mostly two; small; globose; green.

*Stipules.*—On very new growth, dropping off early. (Leaves have tendency to hang on green, longer than other varieties after frost.)

Flower buds: Small to medium; pubescent.

Flowers: First bloom March 1st. Full bloom March 15th. (Blossoms with the Early Hiley variety in Fort Valley, Georgia, area which requires only 750 hours under 45° F. for good production.)

Fruit: Shipping dates comparable to Erly-Red-Fre, and Dixired in Fort Valley, Georgia, area are as follows:

| 1950 | 1951 | 1952 |
|---|---|---|
| Claimed Peach—June 1st | May 14th | May 22d. |
| Dixired—June 7th | May 25th | June 9th. |
| Erly-Red-Fre—June 12th | May 29th | June 9th. |

Large; axial diameter—average 2½ to 2¾ inches.

Transverse in suture plane: 2¼ to 2½ inches.

At right angles to suture plane: 2 to 2¼ inches.

Form: Uniform; oval symmetrical.

Suture: Shallow; distinct; has slight depression towards pistil point.

Ventral surface: Slightly tipped towards apex.

Cavity: Rounded; depth ⅜ inch; width ½ inch.

Apex: Long; pistil point; apical.

Skin: Thin; tough, free from flesh; tendency to crack—none.

Color: Light green to cherry red over color; red splashes. The lightest outside color approaches that of Plate 10, letter K, numeral 5 of the Maerz and Paul Dictionary, shading into the colors of Plates 10, letter B, numeral 7 and Plate 3, letter J, numeral 10 with the darkest shade approaching the color of Plate 6, letter L, numeral 6.

Down: Very moderate and short.

Flesh: White, with slightly red on sunny side. The lightest tone of the flesh approaches that of Plate 9, letter B, numeral 1, shading into the color of Plate 9, letter C, numeral 10 and Plate 9, letter A, numeral 4.

Surface of pit cavity: White with slight green tinge.

Amygdalin: Scant.

Juice: Abundant.

Texture: Fine; firm; melting.

Fibres: Few; fine.

Ripens: Evenly.

Flavor: Subacid.

Aroma: Distinct.

Eating quality: Good.

Stone: Free when mature.

*Size.*—Average length 1⅜ inches.

*Breadth.*—¾ inch; thickness ⅝ inch.

*Form.*—Oval.

*Base.*—Straight, hilum; oval. Apex—acute. Sides—equal; pitted; short grooves throughout. Pits—circular to elongated. Dorsal edge—narrow to a shallow groove. Ventral edge—thin; very slightly winged; ridges interrupted. Tendency to split—very slight. Color of pit—light tan, approaching the color of Plate 9, letter G, numeral 5.

The buds of this new variety of peach have been budded into understock and twenty-five trees have been thus asexually reproduced and have borne peaches of the same characteristic as above set forth. These new trees were developed, and are now growing on the Leman P. Duke farm, 6 miles northwest of Fort Valley, Georgia.

The skin of this new variety has less fuzz than the so-called early varieties and when brushed has the appearance of the plum or apple type of fruit.

The seed of this peach is of small type or size in comparison with the size of the peach. The seed is the first to harden or mature and it has been observed that as the seed matures so does the new peach.

We claim:

The new variety of peach tree as herein disclosed characterized by the fact that it requires less chilling hours for production of buds and blossoms than other so-called early varieties and by ripening earlier than any known freestone type peach; by producing a freestone fruit of unusually large size, having a tendency to a round shape and having uniform ribs on both sides of the seam; the fruit having a skin of intense red, covered with less fuzz than the so-called early varieties and when brushed having the appearance of the plum or apple type of fruit; the fruit meat being of fine texture and generally white blended with pink and red; and the seed of the fruit being of small type in comparison to the size of the fruit.

JOHN F. DUKE, SR.
JOHN F. DUKE, JR.
LEMAN P. DUKE.

References Cited in the file of this patent

UNITED STATES PATENTS

| Number | Name | Date |
|---|---|---|
| Pl. P. 1,021 | Smith | July 10, 1951 |
| Pl. P. 1,022 | Swim | July 24, 1951 |